(12) United States Patent
Cummings et al.

(10) Patent No.: US 7,014,747 B2
(45) Date of Patent: Mar. 21, 2006

(54) DIELECTROPHORETIC SYSTEMS WITHOUT EMBEDDED ELECTRODES

(75) Inventors: Eric B. Cummings, Livermore, CA (US); Anup K. Singh, San Francisco, CA (US)

(73) Assignee: Sandia Corporation, Livermore, CA (US)

( * ) Notice: Subject to any disclaimer, the term of this patent is extended or adjusted under 35 U.S.C. 154(b) by 619 days.

(21) Appl. No.: 09/886,165

(22) Filed: Jun. 20, 2001

(65) Prior Publication Data

US 2004/0026250 A1  Feb. 12, 2004

(51) Int. Cl.
*C25B 11/00* (2006.01)
*C25B 13/00* (2006.01)

(52) U.S. Cl. ................ 204/643; 204/600; 204/450; 204/547

(58) Field of Classification Search .............. 204/600, 204/643, 450, 547
See application file for complete search history.

(56) References Cited

U.S. PATENT DOCUMENTS

| | | | |
|---|---|---|---|
| 3,162,592 A | 12/1964 | Pohl | |
| 4,326,934 A | 4/1982 | Pohl | 204/180 R |
| 4,737,251 A | 4/1988 | Carle et al. | 204/182.8 |
| 4,830,726 A | 5/1989 | Stamato et al. | 204/299 R |
| 5,106,468 A | 4/1992 | Chimenti | 204/180.1 |
| 5,178,737 A | 1/1993 | Lai | 204/182.8 |
| 5,286,434 A | 2/1994 | Slater et al. | 204/182.8 |
| 5,814,200 A | 9/1998 | Pethig et al. | 204/547 |
| 5,837,115 A * | 11/1998 | Austin et al. | 204/450 |
| 5,888,370 A | 3/1999 | Becker et al. | 204/643 |
| 6,071,394 A | 6/2000 | Cheng et al. | 204/547 |
| 6,596,144 B1 * | 7/2003 | Regnier et al. | 204/601 |
| 6,824,664 B1 | 11/2004 | Austin et al. | |

FOREIGN PATENT DOCUMENTS

| | | |
|---|---|---|
| WO | WO 99/33559 | 7/1999 |
| WO | WO 01/37958 | 5/2001 |
| WO | WO 01/37958 A2 * | 5/2001 |

OTHER PUBLICATIONS

Cummings et al., "Dielectrophoretic Trapping without Embedded Electrodes", Proceedings of SPIE, 164-173 (2000).*
Cummings, et al., "Dielectrophoretic Trapping Without Embedded Electrodes," Microfluidic Devices and Systems III, Proceedings of SPIE, Sep. 18-19, 2000, vol. 4177, pp. 164-173.

* cited by examiner

*Primary Examiner*—Ling-Sui Choi
(74) *Attorney, Agent, or Firm*—McDonnell Boehnen Hulbert & Berghoff LLP

(57) ABSTRACT

Method and apparatus for dielectrophoretic separation of particles in a fluid based using array of insulating structures arranged in a fluid flow channel. By utilizing an array of insulating structures, a spatially inhomogeneous electric field is created without the use of the embedded electrodes conventionally employed for dielectrophoretic separations. Moreover, by using these insulating structures a steady applied electric field has been shown to provide for dielectrophoresis in contrast to the conventional use of an alternating electric field. In a uniform array of posts, dielectrophoretic effects have been produced flows having significant pressure-driven and electrokinetic transport. Above a threshold applied electric field, filaments of concentrated and rarefied particles appear in the flow as a result of dielectrophoresis. Above a higher threshold applied voltage, dielectrophoresis produces zones of highly concentrated and immobilized particles. These patterns are strongly influenced by the angle of the array of insulating structures with respect to the mean applied electric field and the shape of the insulating structures.

22 Claims, 9 Drawing Sheets

DIELECTROPHORETIC SYSTEMS WITHOUT EMBEDDED ELECTRODES

STATEMENT OF GOVERNMENT INTEREST

This invention was made with Government support under contract no. DE-AC04-94AL85000 awarded by the U. S. Department of Energy to Sandia Corporation. The Government has certain rights in the invention.

CROSS-REFERENCE TO RELATED APPLICATIONS

Not applicable.

BACKGROUND OF THE INVENTION

The present invention is directed to method and apparatus for dielectrophoresis that eliminates the use of conventional embedded electrodes and substitutes in their place insulating flow structures that create spatially inhomogeneous electric fields that effect dielectric transport. Further, the use of these flow structures provides for dielectrophoretic separations by means of steady applied electric fields, applied alternating electric fields, or combinations thereof.

Electrokinesis and dielectrophoresis are two technologically important particle and fluid transport mechanisms in microscale flow channels. In the former, particle or fluid transport is produced by an applied electric field acting on a fluid or particle immersed in a fluid having a net mobile charge and is widely used as a mechanism for manipulating particles and conveying fluids in Microsystems.

Dielectrophoresis is particle motion produced by an electric field gradient on the induced dipole moment of a particle and the surrounding fluid. Rather than being linear in the applied field as is the case with electrokinesis, the dielectrophoretic potential field experienced by a particle is second order in the local electric field and is proportional to the difference between the particle and fluid polarizabilities. As disclosed, for example, in U.S. Pat. No. 3,162,592, "Materials Separation Using Non-uniform Electric Fields", issued to Pohl; U.S. Pat. No. 5,814,200, "Apparatus for Separation by Dielectrophoresis", issued to Pethig et al.; U.S. Pat. No. 4,326,934, "Continuous Dielectric Cell Classification Method", issued to Pohl; U.S. Pat. No. 6,071,394, "Channelless Separation of Bioparticles on a Bioelectronic Chip by Dielectrophoresis", issued to Cheng et al.; 5,888,370, "Method and Apparatus for Fractionation Using Generalized Dielectrophoretic and Field Flow Fractionation", issued to Becker et al., dielectrophoresis finds extensive application in manipulating, fusing, sorting, and lysing biological materials. However, prior art dielectrophoretic applications have the disadvantage that they require not only the use of networks of embedded electrodes that can be difficult and costly to fabricate to accomplish the desired result but also application of an alternating electric field having zero mean value. Because prior art dielectrophoretic separations apparatus depends upon the use of an applied electric field to effect separation, fluid flow through such an apparatus must be pressure-driven. Electrokinetic or electric field-driven flow cannot be used because of interferences with the electric field produced by the embedded electrodes and its attendant effect upon the separations process. Pressure-driven flow produces more hydrodynamic dispersion of an analyte than electrokinetically driven flow. Moreover, the prior art employs electrodes that produce field gradients in three dimensions, e.g., electrodes deposited on the top, bottom, or both surfaces of a channel. The dielectrophoretic effect decreases away from these electrodes. This decrease limits the maximum depth of the channels over which dielectrophoresis is effective. Channels cannot be made arbitrarily deep to support a desired volumetric flow rate or sample throughput. The depth dependence of the dielectrophoretic effect is also a source of analyte dispersion in a separation.

SUMMARY OF THE INVENTION

Accordingly, the present invention is directed to a method for dielectrophoretic separation of particles and apparatus for practicing same that uses insulating structures disposed in an open or covered fluid flow channels or conduits and bounded by substantially insulating solid or fluid surfaces. The insulating structures can be arranged in a repeating or nearly repeating array to create a non-uniform electric field within a conductive liquid needed for dielectrophoresis. The use of insulating structures to create a non-uniform electric field obviates the need for the complex and difficult-to-fabricate arrays of prior art embedded electrodes. Moreover, the use of multiple electrodes in conventional dielectrophoresis place severe limitations on the channel depth or separation between channel walls because of the shallowness of the field gradient. In the present invention the height of the insulating structures is not affected by that limitation. Further, by eliminating the need for the complex embedded electrode geometries such as used in prior art dielectrophoretic devices to create a non-uniform electric field (cf. U.S. Pat. No. 5,814,200), the present invention does not require the elaborate electric switching means and schemes of prior art embedded electrode geometries (op. cit.). Finally, in contrast to prior art dielectrophoretic separation schemes, both alternating current (AC), wherein the AC can vary in both amplitude and/or period and have a non-zero cyclic average, as well as direct current (DC) electric fields can be utilized in the present invention for particle separation.

The electrodes necessary to generate an electric field, rather than being disposed directly in the fluid flow channels as in prior art devices, can be placed in relatively remote fluid reservoirs that are in fluid communication with the flow channels. Placing electrodes in reservoirs is convenient because: 1) the effects of electrolytic bubble generation that can block narrow fluid flow channels are minimized; 2) electrochemical changes in pH and conductivity are minimized; 3) while not located directly in the flow channel itself, as in prior art dielectrophoretic devices, the electrodes can still be used to produce electrokinetic flow that can be used to move particles through the system; and 4) salt bridges, ultra micro-porous material such as a porous glass material having pores that are sufficiently fine that mass transfer is negligible but that carries the current, such as discussed in U.S. patent application Ser. No. 09/336,535 "Method for Eliminating Gas Blocking in Electrokinetic Pumping Systems" can be used to mitigate mass transfer effects. The electrodes are connected to power supply means that can provide the applied AC or DC voltages necessary to produce the electric fields for particle separation.

In the invention the arrangement of insulating structures produces electric field non-uniformities that, in turn, produce regions of concentrated and rarefied particles that flow as filaments when an electric field is applied across the arrangement. Above a higher threshold of applied electric field, zones of highly concentrated immobilized particles appear. These patterns of flowing filaments of particles and trapped particle zones, which influence particle separation, also depend strongly upon the angle of the axes of the array of insulating structures with respect to the mean applied electric field and the shape of the structures themselves.

Provided the flow channel top and bottom surfaces are quasi-planar, dielectrophoretic transport is independent of depth-wise position, thereby providing for minimal depth-wise dispersion of analytes. Furthermore, the quasi-planar channel can be made shallow to facilitate fabrication or deep to obtain a target volumetric flow rate or sample throughput.

DETAILED DESCRIPTION OF THE INVENTION

Figure 1:
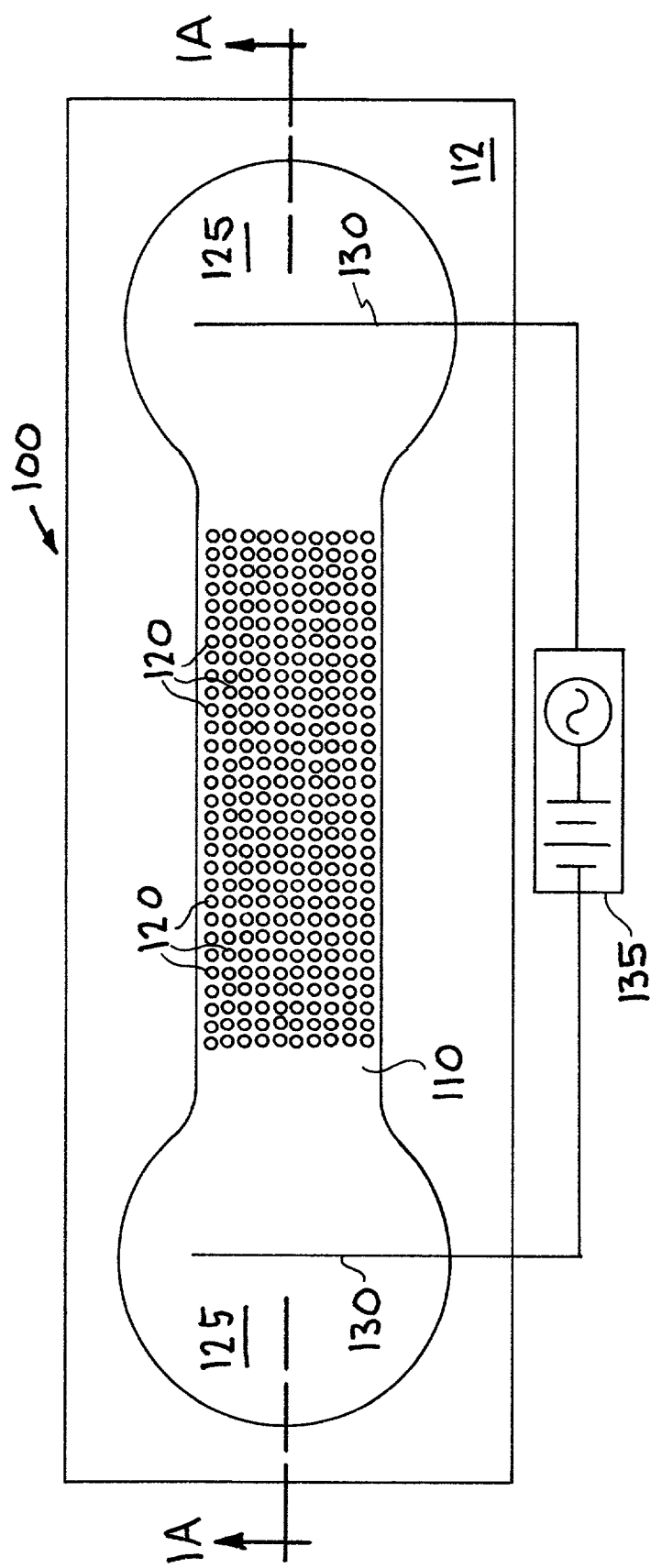
FIG. 1 is an embodiment of the present invention.

The present invention is directed to the use of a plurality of insulating structures arranged within a flow channel of a device for dielectrophoretic separation of particles, wherein the arrangement can be uniform or nonuniform. These insulating structures provide the non-uniform electric field required for the dielectrophoretic separations and replace the embedded electrode structures of conventional devices.

Hereinafter, and throughout the written description of the invention the terms "dielectrophoretic" and "dielectrophoresis" will be abbreviated as DEP, for convenience. The term "particle" is understood to stand for biological as well as non-biological matter generally that can be in the size range of from about 5 nm to 200 μm, such as proteins, DNA, RNA, assemblages of molecules, viruses, plasmids, bacteria, cells or assemblages of cells, protozoans, embryos, or other small organisms, minerals, crystals, colloids, and gas bubbles. The term "spatial separation" is used to describe a process by which particles within a fluid are filtered, concentrated, immobilized, retarded, or advanced relative to the bulk fluid or dissimilar particles. An axis of an array is a direction in which the fluid flow streamlines or electric field lines substantially repeat following an integral number of passages through cells of the array. Principal axes are those that minimize the number of cell passages between repeats of the streamlines. An "applied electric field" relates to the electric field produced by applying a voltage to electrodes in communication to the dielectrophoretic flow system. No statement about the time-history, steadiness, periodicity, or unsteadiness is implied unless explicitly stated. Where not qualified, the applied electric field is regarded as a general unsteady field. The "intensity" of this field is proportional to the temporal mean-square electric field, where the duration of the temporal average is taken, where possible, to be long compared to fluctuation periods, but short compared to periods of actuation, e.g., turning on or off the device. This definition is common and known to those skilled in the art.

In order to understand the invention better, the following brief discussion is provided.

Dielectrophoresis (DEP) is the motion of particles toward or away from regions of high electric field intensity. When an external electric field is applied to a system consisting of a particle suspended in a fluid medium, charges are induced to appear at the particle-fluid interface so as to confer on this polarized particle the properties of an electric dipole. The electrostatic potential of a polarizable particle is minimized in regions of highest electric field intensity. If the particles are immersed in a polarizable fluid, the electrostatic energy of the system is minimized by placing the most polarizable component in the high-field regions. If the particle is more polarizable than the fluid, it will be impelled toward a region of high field intensity (positive dielectrophoresis) or otherwise toward a region of lower field intensity (negative dielectrophoresis). The polarization of particles occurs by a variety of mechanisms having characteristic relaxation times. The frequency variation of the net polarization is a means of obtaining information about or manipulating particles on the basis of their internal and external physical structure. In DEP, the force on a particle and its surrounding medium is proportional to the gradient of the field intensity and is independent of the direction of the electric field. This is in contrast to electrophoresis, the field induced motion of charged particles, wherein the direction of the force on a particle is dependent upon the sign of the charge and the direction of the field.

For a particle to experience either positive or negative DEP it must be subject to a spatially non-uniform electric field. Conventionally, these inhomogeneous fields are produced by the use of various electrode geometries, such as disclosed in U.S. Pat. Nos. 3,162,592 and 5,814,200. However, as will be shown below spatially inhomogeneous fields can be created by the use of insulating structures disposed in flow channels.

In order to illustrate the invention generally and, in particular, to demonstrate the use, effect of insulating structures on DEP, and the interaction between the applied electric field and insulating structures a microfluidic dielectrophoresis device, such as that shown in FIG. 1, was prepared. The device 100 consisted of at least one fluid flow channel or conduit 110 isotropically etched into a glass substrate 112 with a thermally bonded glass cover 115 to enclose the flow channel. In this embodiment flow channel 110 was ≈7 μm deep and had a patterned arrangement or array of insulating structures 120 disposed therein. The insulating structures, formed during the flow channel etching process comprised a plurality of posts or columns of various sizes and shapes that could be arranged in various repetitive or non-repetitive patterns and packing configurations.

Reservoirs 125 were provided at the inlet and outlet ends of each channel. Each reservoir was in fluid communication with a flow channel and each had an electrode 130 in electrical communication therewith. The electrodes were attached to power supply means 135, such as a high voltage power supply capable of supplying either DC or AC power, to provide an electric field in each channel. The outlet reservoirs can provide means for extracting separated particles and the inlet reservoirs can provide means for introducing a fluid suspension of particles to be separated into the patterned channels. In order to illustrate the effect of the insulating structures on electric field lines a suspension of 200 nm diameter fluorescent latex microspheres in an aqueous 1 mM phosphate buffered saline solution maintained at pH 7.7 was supplied to the channel structures through the inlet reservoirs. Examples of various types of DEP separation using the method of the invention are provided below to clarify the principles of this invention and to better understand the Invention; the scope and extent of the invention being defined by the concluding claims.

Filamentary Dielectrophoresis

Because the dielectrophoretic effect is of second order in the applied electric field, it is negligible at suitably low applied fields. In this limit, the dominant particle-transport mechanisms are electrokinesis and diffusion. Advection and electrokinesis do not induce changes in particle concentration for a uniform fluid having a dilute, initially uniform particle concentration. Diffusion, hydrodynamic dispersion, and electrostatic repulsion overwhelm weak dielectrophoresis so no appreciable spontaneous particle concentration gradients form. However, the behavior of particles in mixed DEP and advective/electrokinetic flows changes qualitatively near two threshold applied electric fields: a threshold in which DEP begins to dominate diffusion and a threshold in which DE P becomes comparable to and greater than advection and electrokinesis.

Assuming, as is typically the case, the Peclet number of the particles in the flow is greater than unity, the former threshold occurs at a lower applied electric field than the latter. Above this lower threshold, "filaments" having enhanced or depleted particle concentration appear primarily along flow streamlines. These filaments form when dielectrophoresis begins to produce concentration gradients in the flow. Unlike concentration gradients tangent to streamlines, gradients normal to streamlines are not distorted or dispersed hydrodynamically. Therefore, gradients normal to streamlines can persist even when the DEP effect is too weak to overcome dispersion, so the concentration fields satisfy the relationship ||

$$\nabla c \cdot (u + u_{ek}) << \|\nabla c \times (u + u_{ek})\| \quad (9)$$

where, u accounts for non-electrokinetic components of the flow velocity and $u_{ek}$ accounts for both electroosmosis and electrophoresis. Expression (9) allows one to analyze filamentary dielectrophoresis using a boundary-layer approach. In special cases, e.g., in well-developed flows in uniform periodic arrays, one may approximate that $$\nabla c \cdot (u + u_{ek}) \approx 0 \quad (10)$$

In this approximation, constant-concentration filaments form along streamlines so that the osmotic and electrostatic pressure of the particles balances the effective mean DEP potential along the streamline. Examples of filamentary DEP are illustrated in FIGS. 2–6 below.

Figure 2:
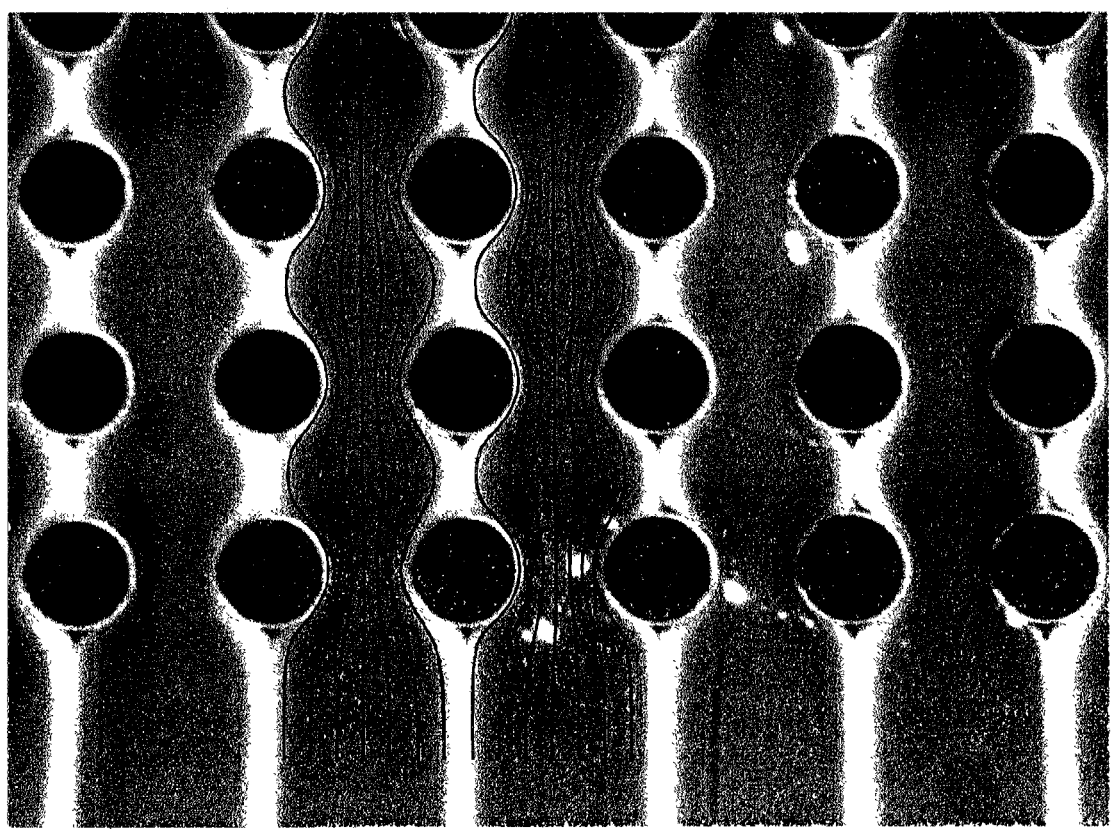
FIG. 2 shows the particle concentration variation in flow past a uniform square array of circular posts.

FIG. 2 shows the particle concentration variation in flow past a uniform square array of circular posts 56 posts long and 16 posts wide. The 33 μm diameter posts are arranged on 63 μm centers. In this example the electric field of 25 V/mm is oriented in alignment with an array of posts, a principal axis of the array. For purposes of illustrating their relationship to the particle filaments, electrokinetic flow streamlines are superimposed on the image. The gray scale of the image shows the relative intensity of particle fluorescence and is thus a measure of particle concentration. The thin bright border around each post is strong specular reflection of the illumination light and is not a fluorescence signal. In the figures below all flows are from the top of the figure to the bottom and produced by a voltage applied to remote electrodes.

It can be seen in FIG. 2 that the particle concentration varies little in the core flow between the post columns. Approaching the columns, the particle concentration increases several-fold. Near the stagnation streamline down the center of the column, the concentration dips significantly. This pattern of particle persists as the streamlines leave the post array, supporting approximation (9) everywhere and approximation (10) within the post array.

Figure 3:
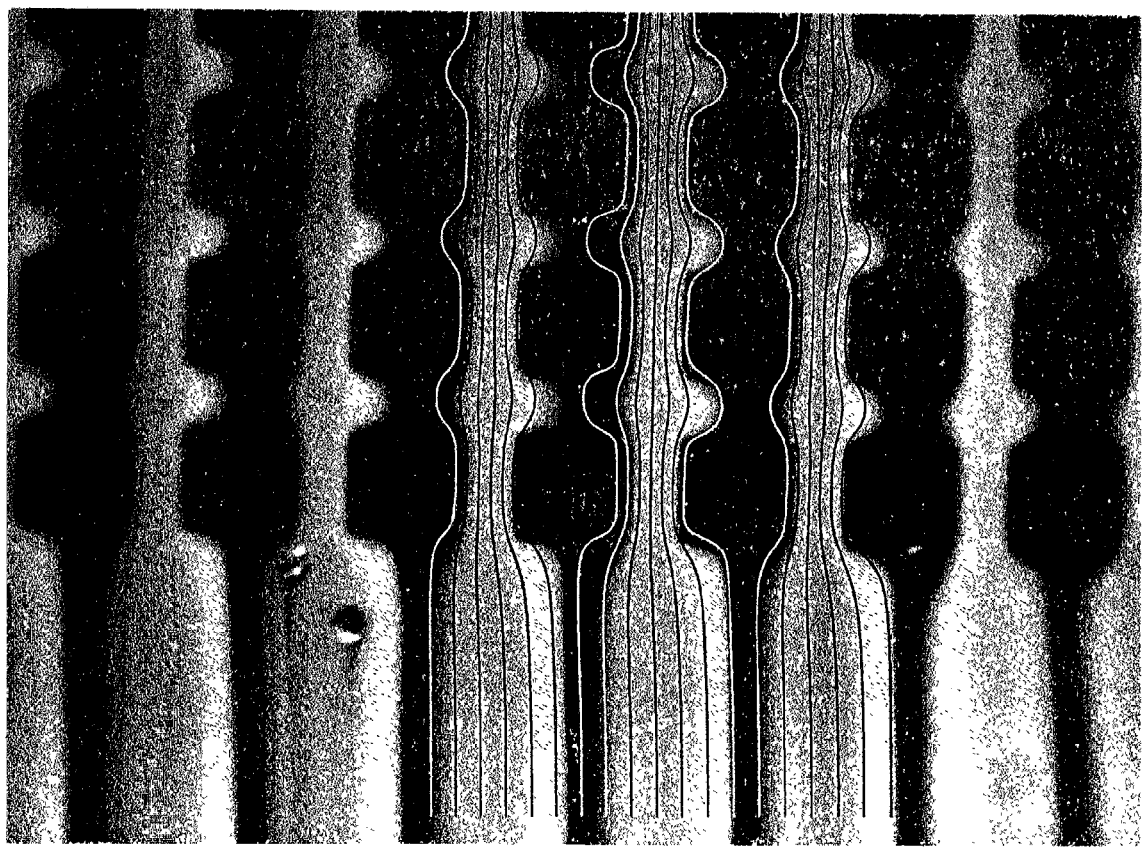
FIG. 3 shows the particle-concentration variation in particle flow past the end of a uniform square array of square posts.

FIG. 3 shows the particle-concentration variation in particle flow past the end of a uniform square array of square posts having sides 36 μm long and arranged on 63-μm centers. The properties of the array are otherwise the same as those of the previous array. However, in contrast to the example shown in FIG. 2, the ≈80 V/mm mean field is applied at an angle of 1.6° with respect to the principal axis of the array of posts. This angle of attack produces filaments that are slightly asymmetrical with respect to the columns of square posts. Again, the filaments align with the calculated electrokinetic flow streamlines. In this case, the large stagnant regions of the flow between the posts are highly depleted of particles. There is no evidence of filaments having significantly enhanced concentration as seen in FIG. 2. In fact, the difference between these images is a striking demonstration of the importance of post shape in the dielectrophoretic behavior of an array.

Figure 4:
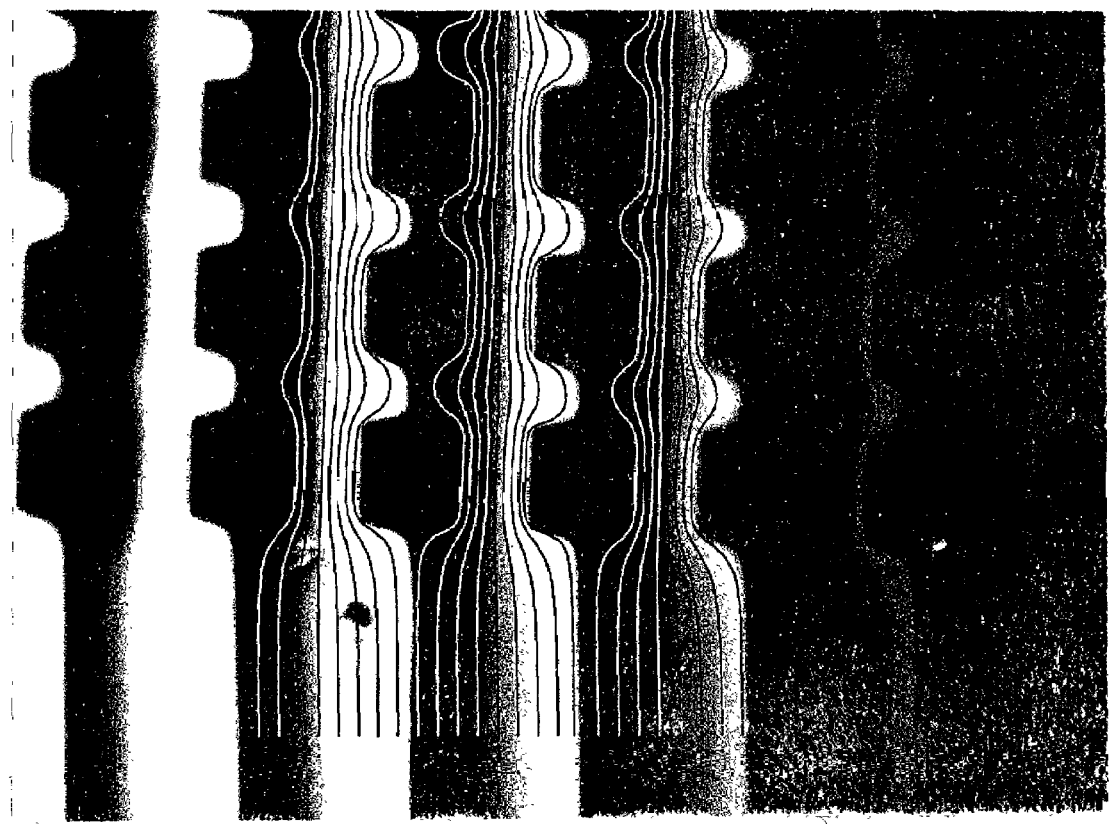
FIG. 4 shows the particle-concentration fields at the base of the same array as in FIG. 3 but with the electric field applied at an angle of 2.3° with respect to the principal axis of the array of posts.

FIG. 4 shows the particle-concentration fields at the base of the same array as in FIG. 3 but with the electric field applied at an angle of 2.3° with respect to the principal axis of the array of posts. The asymmetrical concentration gradient is seen to be dramatically steep toward the left of the post columns and relatively diffuse toward the right. The columns of posts produce a dielectrophoretic potential barrier that the fluid, but not the particles, can cross.

Figure 5:
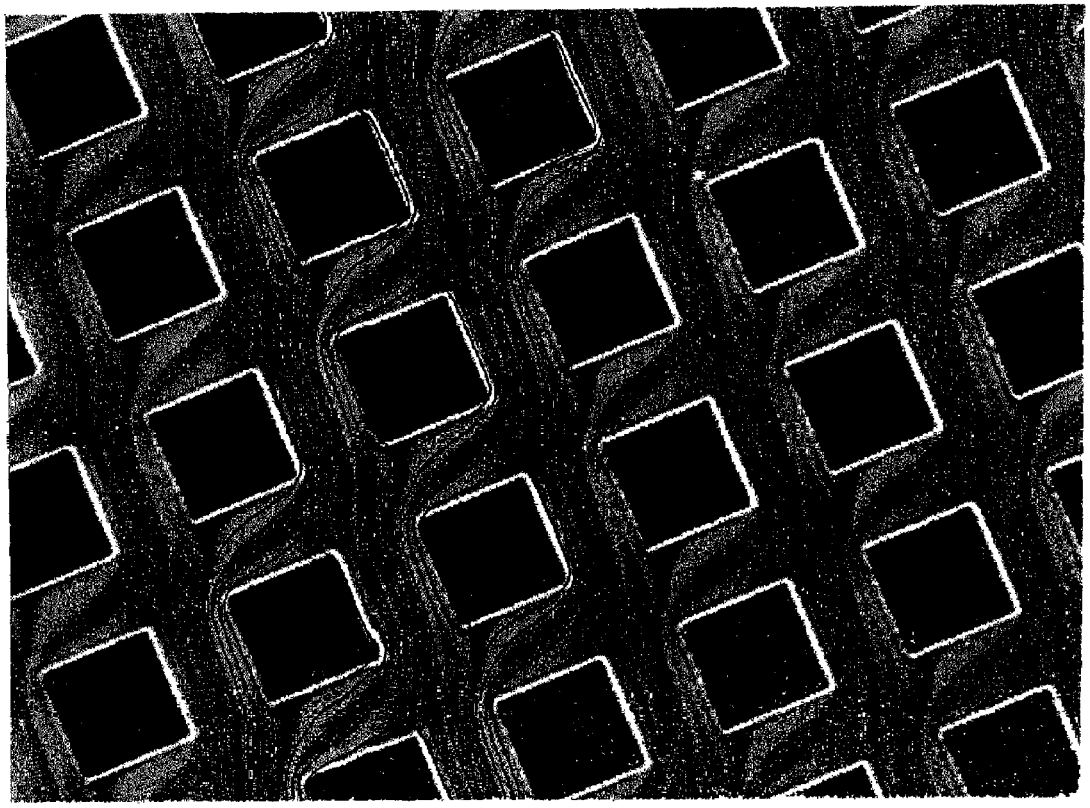
FIG. 5 shows the particle-concentration field in the center of an array of posts but with the electric field applied at an angle of 20.5° with respect to the principal axis of the array of posts.

FIG. 5 shows the particle-concentration field in the center of an array of posts with the same properties as those of FIGS. 3 and 4 but with the principal axis of the array oriented at 20.5° with respect to the applied electric field of ≈80 V/mm. In this flow, the variation in concentration is much weaker than in the previous examples because of the limited cooperative effect of the posts. The concentration gradients are only weakly coherently enhanced by the array since the streamline patterns approximately repeat after an offset of 5 rows and 2 columns rather than the offset of approximately 1 row in the previous figures.

Figure 6:
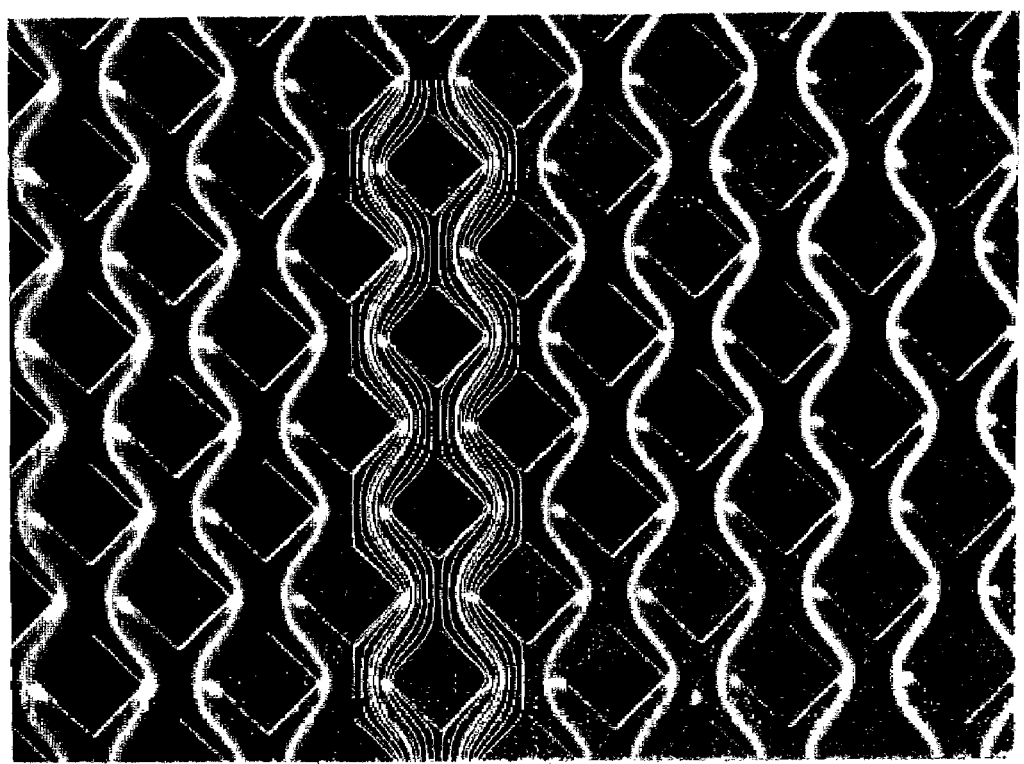
FIG. 6 shows the particle-concentration field in the center of a square array of posts with an electric field applied at angle of ≈45.3° with respect to the principal axis of the array (0.3° from a secondary axis of the array).

FIG. 6 shows the particle-concentration field in the center of a square array similar to those in the previous figures but with an electric field of 80 V/mm applied at angle of ≈45.3° with respect to the principal axis of the array (≈0.3° with respect to a secondary axis). In this example, the streamline pattern approximately repeats after an offset of 1 row and 1 column. The diagonal orientation of the square posts creates a large electric field concentration at the left and right vertices. The dielectrophoretic effect adds coherently in the array to produce a filament of high particle concentration that travels down the streamline at center of the channels. This effect significantly reduces the interactions of the particles with the posts. Similar arrays have been proposed and used (cf. B. He et al., "Fabrication of nanocolumns for liquid chromatography, Anal. Chem., 70, 3790, 1996 and F. Regnier, "Microfabricated monolith columns for liquid chromatography: Sculpting supports for liquid chromatography", HRC-J. High Res. Chrom., 23, 19, 2000) for electrochromatography, where sharply reduced surface interactions of positive dielectrophoretic molecules may affect separations.

Figure 9:
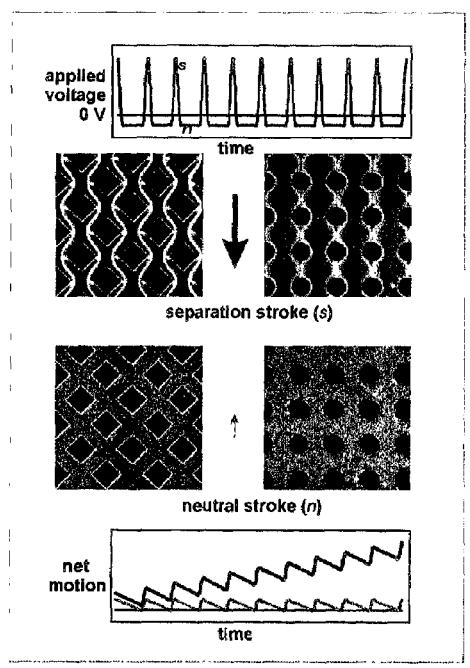
FIG. 9 shows examples of cyclic separations based upon filamentary DEP in circular- and square-post arrays.

The bright regions near the left and right vertices of the posts show the onset of particle trapping. As time progressed, these regions grew as shown in FIG. 9 below.

Trapping Dielectrophoresis

The second threshold in mixed dielectrophoretic and electrokinetic flows occurs at an applied electric field in which the local DEP force exceeds the electrokinetic and hydrodynamic drag force. Above this threshold, regions appear where particles are "trapped" by the DEP field. The number of particles in the trap grows in time until the applied field stops, the particles fill the region of the trap, or the presence of particles modifies the trap by perturbing the electric field and electroosmotic flow.

Figure 7:
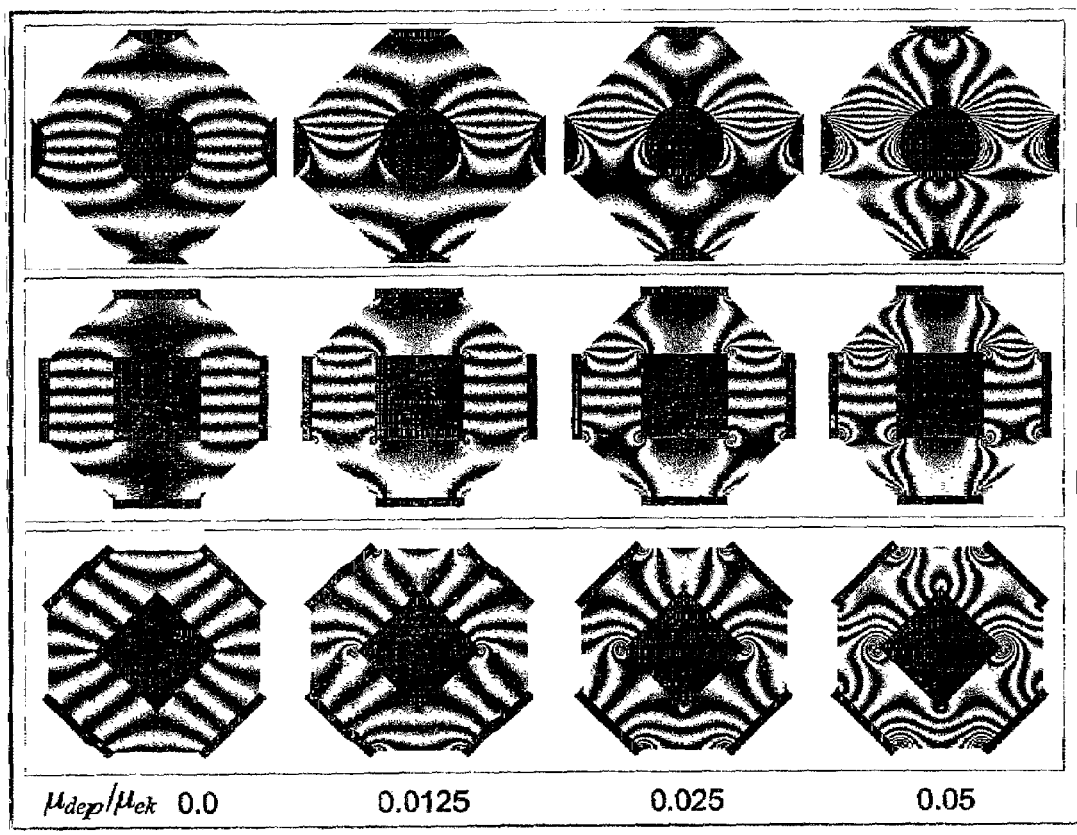
FIG. 7 is a graphical representation of the combined electrokinetic and dielectrophoretic potential, ψ, from within a cell comprising three kinds of uniform arrays.

FIG. 7 is a graphical representation of the combined electrokinetic and DEP potential, $\psi$, within unit cells comprising three kinds of uniform arrays. The flow in these arrays is from top to bottom Isopotentials are lines of constant phase along a fringe. Adjacent fringes correspond to one tenth of the cell unit-potential difference. The potential difference across the cell, the size of the cell and the electrokinetic mobility of the particles are normalized to unity. Because of the substantial absence of inertia, particles travel in paths normal to the isopotentials. The left-most images show the undisturbed electrokinetic potential within the arrays. The other images show the distortion of the combined electrokinetic and DEP potentials of particles having a relative DEP mobility of 0.0125, 0.025, and 0.05. Trapping zones (for positive DEP particles) appear in the lower-left and right sides of the circular posts. Smaller zones appear for the on-axis square array. The 45° square array shows the formation of strong and sizable trapping zones even at low DEP mobility. The depth of the potential well of the traps is proportional to the number of fringes that curve around the well.

Figure 8:
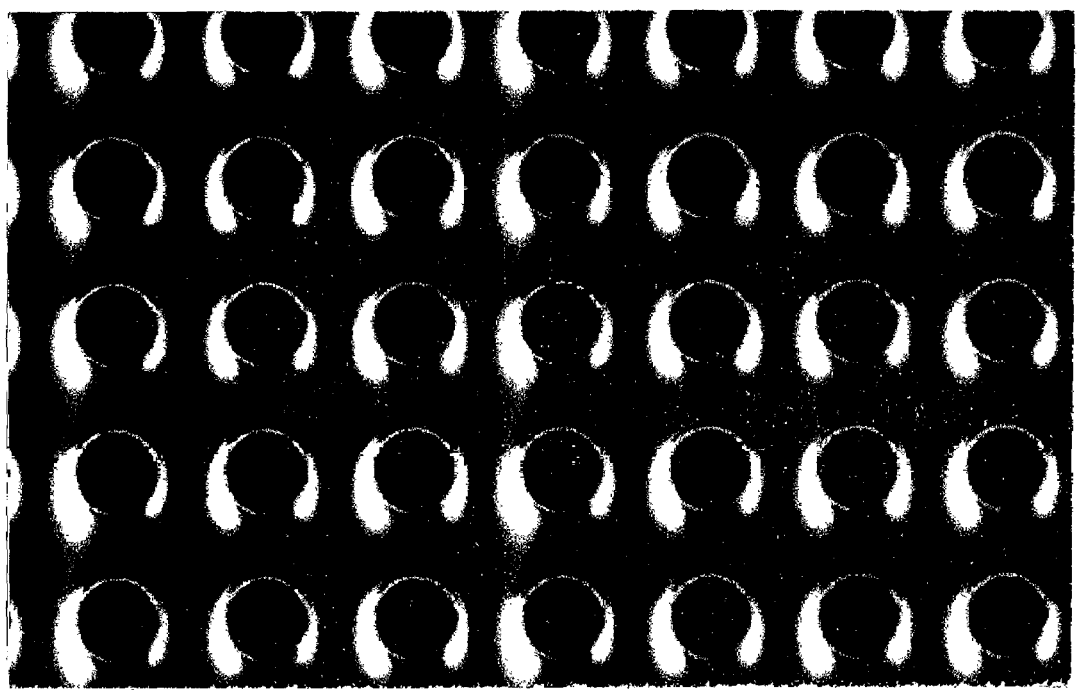
FIG. 8 shows the flow in the interior of a uniform square array of circular posts at an applied electric field of ≈100 V/m.

FIG. 8 shows the flow in the interior of the array of FIG. 2, however, at an applied electric field of ≈100 V/m. The bright regions to the lower left and right of the circular posts contain trapped particles. Relatively weak fluorescence from concentrated filaments is evident along the streamlines near the regions of trapped particles. This image was recorded after the trapped regions had apparently reached steady state, about 5 seconds after the electric-field forcing started. The zones where particles are trapped are consistent with the location of the wells in the combined potential fields in FIG. 7.

Under conditions where particle trapping occurs, i.e., where the electric field applied to a fluid flowing through an array of insulating posts or columns is equal to or greater than some minimum value, that can depend upon the shape of the insulating structures as well as the composition of the fluid and particles, the particles can be assumed to be effectively immobilized within traps formed around the insulating posts disposed in the flow channel (cf. FIG. 8). Dispersive separations can be performed by ramping the amplitudes of the alternating or quasi-steady components of the applied electric field and consequently the depth of the traps. This ramping can be monotonic, analogous to a gradient elution in chromatography, or repeated.

Arrays such as that shown in FIG. 8 can also be used as gated traps or particle concentrators by applying an electric field to collect particles having a dielectrophoretic mobility above the trapping threshold produced by that field. When the applied field is lowered or made zero, the particles can be released in a concentrated stream, possibly to a secondary flow channel. A similar device that concentrates particles, while spatially segregating them by their dielectrophoretic mobility can be made by tapering the channel to concentrate the electric field at one end or by changing the post dimensions or shape across the array or a combination of these two methods.

Matter can be transported by cyclic forcing fields provided the matter undergoes a net displacement during a forcing cycle. If the mobility of the matter in the field is independent of the magnitude of the field (linear or field-linear transport), the net material displacement during a cycle is proportional to the cyclic average of the field. For example, a particle with an electric-field-independent electrophoretic mobility undergoes no net electrophoretic transport when acted upon by an alternating electric field with a zero cyclic average. If the mobility of the matter varies with the applied field (nonlinear or field-nonlinear transport), additional transport mechanisms exist. For matter whose mobility varies with the absolute magnitude of the applied field, nonlinear transport can occur when the fields are applied asymmetrically about zero during a cycle. By way of example, pulsed-field electrophoresis exploits the dependence of electrophoretic mobility on the magnitude of the electric field via field-induced molecular alignment. This alignment effect increases with molecular length, so asymmetrical forcing can be used for example to separate or filter DNA strands on the basis of their length (cf. U.S. Pat. No. 4,737,251 "Field-inversion Gel Electrophoresis" issued to Carle et al., U.S. Pat. No. 4,830,726 "Separation of Large DNA Molecules in Alternating Asymmetric Fields" issued to Stamato et al., and U.S. Pat. No. 5,178,737 "Electrophoretic Resolution of Single Strand DNA by Asymmetric Fields" issued to Lai) and to separate large organic molecules from small ionic molecules(cf. U.S. Pat. No. 5,106,468, "Electrophoretic Separation", issued to Chimenti and U.S. Pat. No. 5,286,434 "Processes for the Preparation and Separation of Macromolecules" issued to Slater et al.). Cyclic transport is useful in cases where: 1) the field-linear transport is undesirable, 2) the desired mechanism of differentiation appears in field-nonlinear transport, and 3) practical considerations prevent the use of a fixed-length, single-pass column. These practical considerations include geometrical limitations, the desire for system flexibility to optimize rate, efficiency, resolution, etc.

A cyclic separation can be conceptually decomposed into four steps, that in practice may not be completely distinct:

1. Formation of a mobility-modifying structure, e.g., molecular alignment, formation of DEP filaments and traps;

2. Propagation of flow with modified particle mobility, e.g., electrophoresis;

3. Destruction of mobility-modifying structure or formation of different structures; and 4. Propagation of flow with unperturbed or alternate mobility, e.g., electrophoresis in the reverse direction.

As described earlier, The present invention provides a novel mechanism for modifying the effective electrophoretic mobility of a particle with an array of obstacles or posts. Both filamentary and trapping DEP phenomena can be utilized in a cyclic-transport system. In many applications of DEP, an alternating electric field is employed to generate a low-frequency or near steady DEP force. In contrast, the cyclic forcing here results from periodically changing the magnitude of this near-steady DEP force.

FIG. 9 shows examples of cyclic separations based upon filamentary DEP in circular- and square-post arrays. Depending on the geometry of the posts, positive DEP particles can be advanced or retarded compared to dielectrophoretically neutral particles. In the first and second steps of the cycle, filaments form and propagate as shown in the top inset images. In the third and fourth steps, the filaments disappear and the particles flow without bias back up the array as shown in the lower inset image. A cycle having a non-zero average applied field can be used to superimpose any desired field-linear particle transport.

Figure 10:
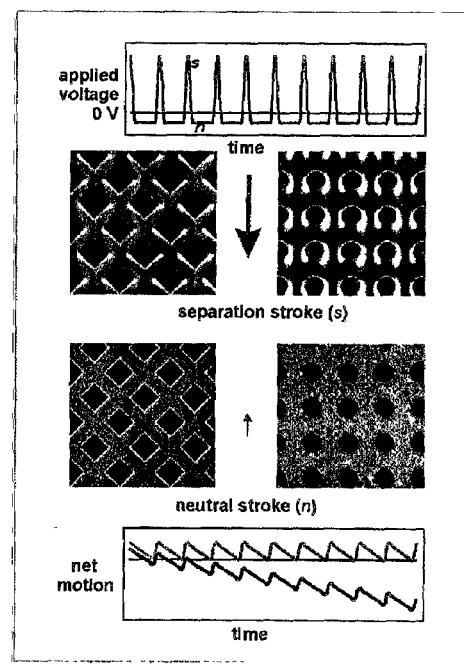
FIG. 10 illustrates cyclic separations based upon trapping DEP.

FIG. 10 illustrates cyclic separations based upon trapping DEP. In the first and second steps of the cycle, the particles enter traps and are immobilized or severely retarded while the unaffected fluid flows as shown in the upper inset image. In the third and fourth steps, the traps are released and both the particles and fluid flow freely back up the array as shown in the lower inset image.

The present invention provides method and apparatus for purely DC electric field-driven dielectrophoresis of particles in microfluidic systems with electrokinetic flow. The use of AC electric field-driven dielectrophoresis, wherein the AC electric field can vary in amplitude and period and/or have a non-zero cyclic average is also contemplated by this invention as well as combinations of DC and AC electric fields. The systems disclosed herein are noteworthy for their simplicity of fabrication. No diffraction-limited lithography, embedded electrodes or small/high-aspect-ratio structures are required to produce significant effects on particles in the range of 200-nm diameter. Consequently, these systems can be produced by methods well known in the art such as, but not limited to, casting, photopolymerization, isotropic and anisotropic glass or alumina etching, polymer etching, LIGA, and other mass-fabrication techniques. While the invention was illustrated by the use of glass substrates, polymer materials such as polymethylmethacrylate, polycarbonate, fluorocarbons, polyolefins, and epoxies can be used as substrate material.

The formation of spatially inhomogeneous particle concentration fields by both filamentary and trapping DEP (discussed above) is a process of spatial separation of particles that can be exploited directly for concentration, filtration, and fractionation of particles. Furthermore, dielectrophoresis in arrays of posts whose geometry varies in a direction that is not aligned with the mean electric field can produce dielectrophoretic transport that is also not aligned with the mean electric field. This transport produces a polarizability-dependent particle-flow direction through the array. Applications of this technique can include sorting viable or normal cells from dead or abnormal cells, prefiltration or sorting of background particulates from target particles, etc.

As discussed above, the method of filamentary dielectrophoresis can be used to enhance or deplete spatially the number density of particles in a stream, with applications to flow-through concentration or filtration. Furthermore, preferred streamlines or concentrated filaments temporally disperse the time of flight of particles down the array on the basis of their dielectrophoretic mobility. This dispersion can be used for separation by dielectrophoretic mobility. Trapping dielectrophoresis can reversibly concentrate particles to high density in zones of a flow-through system, also with applications to concentration, filtration, and separation. Because dielectrophoresis is nonlinear in the applied electric field, the magnitude of the effect is tunable by simply changing the amplitude and/or period of the applied electric field (or the sinusoidal and constant components of the applied field in an AC/DC dielectrophoretic system). This adjustability gives dielectrophoresis an advantage over, for example, purely mechanical filters, which can clog and electrochromatographic separation columns, in which the interaction potential of the analytes and the stationary phase is fixed for a given buffer.

The impact of the post shape and angle of the array with respect to the applied fields on the concentration fields is remarkable, with square posts producing essentially the opposite effect from circular posts. This observation supports the intuitive notion that the shape and arrangement of posts in an array can be optimized to enhance a particular behavior, something that is not possible in a randomly packed medium. The invention is illustrated by the use of square or circular posts. However, the boundary edges of the insulating structures, in horizontal cross-section, can all be derived from components of simple shape primitives such as straight lines, cusps, concave and/or convex curves, and acute angles of which square and circular posts are examples. Moreover, these simple shape primitives can be used either singly or in combination to enhance the desired transport. The insulating structures in a particular arrangement can also be of more than one size.

The insulating structures or posts can be joined or overlapping in such a way as to make a solid wall through which particles cannot pass. Such posts can be etched so that the cross-sectional plane is oriented into the substrate. The posts need not be two-dimensional or intersect with either top or bottom bounding surfaces of the fluid. For example, the posts can be hemispherical bumps on a substrate surface, substantially cylindrical structures that stop short of the top surface and thereby create a field concentration above them, or posts that extend through the liquid-gas interface in a flow channel.

The function of the shape primitives varies with the orientation of the primitive with respect to the applied field and the other primitives comprising the post and neighboring posts. By way of example, a convex curve centered near right-angles to the applied field produces a relatively weak field concentration over a region approximately equal to the circular radius, useful for making high-capacity DEP traps and concentrated particle filaments, but requiring higher threshold fields than the sharp corner. A straight line is comparatively inactive but serves to link different shape primitives. A sharp corner pointing upstream or downstream is a flow splitter and combiner that produces a relatively small flow-stagnation/low-electric field region. A sharp corner pointing cross-stream produces a marked field concentration at the tip allowing the trapping of particles at relatively low applied fields. A cusped corner enhances the behavior of the sharp corner, in both orientations discussed above, at an increase in manufacturing difficulty. A cusp and, to a lesser extent, sharp corner produce a dielectrophoretic force gradient local to the tip which can be used to stretch, tear apart, or lyse particles having a diameter comparable or greater than the tip radius. A concave cutout reduces the electric field within the cutout and is useful for creating positive dielectrophoretic barriers or negative dielectrophoretic traps.

As evidenced by FIG. 5, the magnitude of gradients produced dielectrophoretically decreases when there is little or no coherent forcing. While filamentary dielectrophoretic can be ignored in theoretical studies of particle transport and separations in random media, this approximation is not necessarily justified in patterned or structured media.

The foregoing is intended to be illustrative of the present invention and is provided for purposes of clarity and understanding of the principles of this invention. Many other embodiments and modifications can be made by those of skill in the art without departing from the spirit and scope of the invention as defined in the following claims.

We claim:

1. An apparatus for dielectrophoretic separation, comprising:
   a fluid flow channel disposed on a substrate, wherein said fluid flow channel is provided with fluid inlet and outlet means in fluid communication with said fluid flow channel, and wherein said fluid flow channel has a plurality of insulating structures disposed therein;
   electrodes in electric communication with each fluid inlet and outlet means, wherein the electrodes are positioned to generate a spatially non-uniform electric field across the plurality of insulating structures, and wherein the spatially non-uniform electric field exerts a dielectrophoretic force on a sample undergoing separation; and
   power supply means connected to said electrodes to generate an electric field within said fluid flow channel, wherein electroosmotic flow of a fluid in said fluid flow channel is not suppressed.

2. The apparatus of claim 1, wherein said fluid flow channel is an open channel.

3. The apparatus of claim 1, wherein the substrate is a polymer material.

4. The apparatus of claim 1, wherein the plurality of insulating structures is arranged in an array.

5. The apparatus of claim 1, wherein at least a portion of the cross-sectional shape of the insulating structures in the plane of fluid flow is composed of a circle, a straight line, a cusp, a concave curve, a convex curve, or an acute angle, or combinations thereof.

6. The apparatus of claim 5, wherein the insulating structures comprise circular posts.

7. The apparatus of claim 5, wherein the insulating structures are square posts.

8. The apparatus of claim 1, wherein the insulating structures are joined together.

9. The apparatus of claim 1, wherein the electric field is a substantially constant applied electric field.

10. The apparatus of claim 1, wherein the electric field varies in amplitude and period.

11. The apparatus of claim 1, wherein the electric field has a non-zero cyclic average.

12. The apparatus of claim 1, wherein the electric field is a combination of an electric field that is substantially constant and an electric field that varies in amplitude and period.

13. The apparatus of claim 1, wherein the electric field is aligned at an angle with respect to the array of posts.

14. An apparatus for concentrating and spatially segregating particles, comprising:
   a fluid flow channel disposed on a substrate, wherein said fluid flow channel is provided with first and second ends, and fluid inlet and outlet means in fluid communication with the first and second ends, and wherein said flow channel has a plurality of insulating structures disposed therein;
   electrodes in electric communication with each fluid inlet and outlet means, wherein the electrodes are positioned to generate a spatially non-uniform electric field across the plurality of insulating structures, and wherein the spatially non-uniform electric field exerts a dielectrophoretic force on a sample undergoing separation; and
   power supply means connected to said electrodes to generate an electric field within said fluid flow channel, wherein the second end of said fluid flow channel is tapered to concentrate the electric field, and wherein electroosmotic flow of a fluid in said fluid flow channel is not suppressed.

15. The apparatus of claim 14, wherein said fluid flow channel is an open channel.

16. The apparatus of claim 14, wherein the substrate is a polymer material.

17. The apparatus of claim 14, wherein the plurality of insulating structures is arranged in an array.

18. The apparatus of claim 17, wherein the array of insulating structures is shaped so as to concentrate the electric field.

19. An apparatus for dielectrophoretic separation, comprising:
   a fluid flow channel disposed on a substrate, wherein said fluid flow channel is provided with fluid inlet and outlet means in fluid communication with said fluid flow channel, and wherein said fluid flow channel has a plurality of insulating structures disposed therein;
   electrodes in electric communication with each fluid inlet and outlet means, wherein the electrodes are positioned to generate a spatially non-uniform electric field across the plurality of insulating structures, and wherein the spatially non-uniform electric field exerts a dielectrophoretic force on a sample undergoing separation; and
   power supply means connected to said electrodes to generate an electric field within said fluid flow channel, wherein the insulating structures comprise circular posts.

20. The apparatus of claim 19, wherein the plurality of insulating structures is arranged in an array.

21. An apparatus for dielectrophoretic separation, comprising:
   a fluid flow channel disposed on a substrate, wherein said fluid flow channel is provided with fluid inlet and outlet means in fluid communication with said fluid flow channel, and wherein said fluid flow channel has a plurality of insulating structures disposed therein;
   electrodes in electric communication with each fluid inlet and outlet means, wherein the electrodes are positioned to generate a spatially non-uniform electric field across the plurality of insulating structures, and wherein the spatially non-uniform electric field exerts a dielectrophoretic force on a sample undergoing separation; and
   power supply means connected to said electrodes to generate an electric field within said fluid flow channel, wherein the insulating structures comprise square posts having sides that are parallel to the fluid flow channel.

22. The apparatus of claim 21, wherein the plurality of insulating structures is arranged in an array.

* * * * *